(12) United States Patent
Hain et al.

(10) Patent No.: US 7,452,374 B2
(45) Date of Patent: Nov. 18, 2008

(54) AV GRAFTS WITH RAPID POST-OPERATIVE SELF-SEALING CAPABILITIES

(75) Inventors: Matt Hain, Wayne, NJ (US); Tamara King, Haskell, NJ (US)

(73) Assignee: Maquet Cardiovascular, LLC, San Jose, CA (US)

( * ) Notice: Subject to any disclaimer, the term of this patent is extended or adjusted under 35 U.S.C. 154(b) by 0 days.

(21) Appl. No.: 10/422,118

(22) Filed: Apr. 24, 2003

(65) Prior Publication Data

US 2004/0215337 A1 Oct. 28, 2004

(51) Int. Cl.
*A61F 2/06* (2006.01)
(52) U.S. Cl. ............ 623/1.44; 623/1.32; 623/1.49
(58) Field of Classification Search ........ 623/1.32–1.54
See application file for complete search history.

(56) References Cited

U.S. PATENT DOCUMENTS

| | | | |
|---|---|---|---|
| 3,479,670 A | 11/1969 | Mendell | |
| 3,953,566 A | 4/1976 | Gore | |
| 4,047,252 A | 9/1977 | Liebig et al. | |
| 4,304,010 A | 12/1981 | Mano | |
| 4,550,447 A | 11/1985 | Seiler, Jr. et al. | |
| 4,619,641 A | 10/1986 | Schanzer | |
| 4,652,263 A | 3/1987 | Herweck et al. | |
| 4,718,907 A | 1/1988 | Karwoski et al. | |
| 4,878,908 A | 11/1989 | Martin et al. | |
| 4,892,539 A | 1/1990 | Koch | |
| 5,061,276 A | 10/1991 | Tu et al. | |
| 5,116,360 A * | 5/1992 | Pinchuk et al. | ......... 623/11.11 |
| 5,163,951 A | 11/1992 | Pinchuk et al. | |
| 5,178,630 A | 1/1993 | Schmitt | |
| 5,192,310 A | 3/1993 | Herweck et al. | |
| 5,370,682 A | 12/1994 | Schmitt | |
| 5,411,550 A | 5/1995 | Herweck et al. | |
| 5,456,711 A | 10/1995 | Hudson | |
| 5,509,931 A | 4/1996 | Schmitt | |
| 5,628,782 A | 5/1997 | Myers et al. | |
| 5,700,287 A | 12/1997 | Myers et al. | |
| 5,716,395 A * | 2/1998 | Myers et al. | ........... 623/1.5 |
| 5,728,103 A | 3/1998 | Picha et al. | |
| 5,732,572 A | 3/1998 | Litton | |

(Continued)

FOREIGN PATENT DOCUMENTS

EP 0 492 481 A1 7/1992

(Continued)

OTHER PUBLICATIONS

Wilson et al., Slide Forum-Renal 5, "A Corethane/Polyester Composite Vascular Prosthesis for Vascular Access", "Comparison with Expanded Polytetrafluoroethylene Grafts in a Canine Model", 4535 ASAIO Journal, 41(1995) Jul./Sep., No. 3, Hagerstown, MD, US, pp. M728-M734.

*Primary Examiner*—Bruce E. Snow
(74) *Attorney, Agent, or Firm*—Hoffmann & Baron, LLP (57) ABSTRACT

The invention provides a self-sealing arteriovenous graft including a tube having a polymeric inner layer defining a lumen through which blood may flow and an outer textile layer. The outer textile layer is concentrically disposed about the inner layer. Furthermore, an intermediate self-sealing layer is concentrically positioned between the inner and outer layers. The self-sealing layer includes a biocompatible polymer.

16 Claims, 5 Drawing Sheets

U.S. PATENT DOCUMENTS

| | | | |
|---|---|---|---|
| 5,741,325 A | 4/1998 | Chaikof et al. | |
| 5,741,332 A | 4/1998 | Schmitt | |
| 5,755,775 A | 5/1998 | Trerotola et al. | |
| 5,769,882 A * | 6/1998 | Fogarty et al. | 128/898 |
| 5,800,512 A | 9/1998 | Lentz et al. | |
| 5,840,240 A | 11/1998 | Stenoien et al. | |
| 5,861,033 A | 1/1999 | Martakos et al. | |
| 5,866,217 A | 2/1999 | Stenoien et al. | |
| 5,879,320 A | 3/1999 | Cazenave | |
| 5,904,967 A | 5/1999 | Ezaki et al. | |
| 5,910,168 A | 6/1999 | Myers et al. | |
| 5,911,753 A | 6/1999 | Schmitt | |
| 5,913,894 A | 6/1999 | Schmitt | |
| 5,916,264 A | 6/1999 | Von Oepen et al. | |
| 5,931,865 A | 8/1999 | Silverman et al. | |
| 5,948,018 A | 9/1999 | Dereume et al. | |
| 5,957,974 A | 9/1999 | Thompson et al. | |
| 5,976,192 A | 11/1999 | McIntyre et al. | |
| 6,001,125 A | 12/1999 | Golds et al. | |
| 6,056,970 A * | 5/2000 | Greenawalt et al. | 424/426 |
| 6,090,137 A | 7/2000 | Schmitt | |
| 6,102,884 A | 8/2000 | Squitieri | |
| 6,221,099 B1 | 4/2001 | Andersen et al. | |
| 6,261,255 B1 | 7/2001 | Mullis et al. | |
| 6,261,257 B1 | 7/2001 | Uflacker et al. | |
| 6,319,279 B1 * | 11/2001 | Shannon et al. | 623/1.44 |
| 6,331,191 B1 | 12/2001 | Chobotov | |
| 6,361,556 B1 | 3/2002 | Chuter | |
| 6,428,571 B1 * | 8/2002 | Lentz et al. | 623/1.4 |
| 6,440,166 B1 | 8/2002 | Kolluri | |
| 6,488,705 B2 | 12/2002 | Schmitt et al. | |
| 6,534,084 B1 * | 3/2003 | Vyakarnam et al. | 424/443 |
| 6,547,820 B1 * | 4/2003 | Staudenmeier | 623/1.49 |
| 6,709,455 B1 | 3/2004 | Chouinard | |
| 2003/0017775 A1 * | 1/2003 | Sowinski et al. | 442/315 |
| 2003/0139806 A1 * | 7/2003 | Haverkost et al. | 623/1.33 |
| 2004/0054406 A1 * | 3/2004 | Dubson et al. | 623/1.39 |
| 2004/0122507 A1 * | 6/2004 | Henderson | 623/1.27 |

FOREIGN PATENT DOCUMENTS

| | | |
|---|---|---|
| GB | 567641 | 2/1945 |
| GB | 568177 | 3/1945 |
| GB | 571657 | 9/1945 |
| GB | 624987 | 6/1949 |
| WO | WO 02/100454 A1 | 12/2002 |

* cited by examiner

AV GRAFTS WITH RAPID POST-OPERATIVE SELF-SEALING CAPABILITIES

FIELD OF THE INVENTION

This invention relates to an arteriovenous (AV) graft, and more particularly, to a flexible self-sealing graft having increased hemostatic properties and suture retention strength.

BACKGROUND OF THE INVENTION

Dialysis treatment of individuals suffering from renal failure requires that blood be withdrawn and cycled through a dialysis machine that performs the function of the failed kidneys. This process, termed hemodialysis, must be repeated periodically and thus requires repeated puncture wounds using dialysis needles. Moreover, dialysis requires a relatively rapid blood flow rate so the dialysis needle is relatively large. Frequent puncturing of native vessels with large bore needles can cause trauma and eventually a loss of patency.

A common technique to provide vascular access for hemodialysis, therefore, is to connect a prosthetic (AV) graft or shunt between an artery and a vein in, for example, the arm.

Conventional AV grafts are often constructed of polymer material such as expanded polytetrafluoroethylene (ePTFE). ePTFE grafts are generally not self-sealing when punctured and usually require implantation for two or more weeks prior to puncture so that a layer of fibrotic tissue has an opportunity to attach to the outside surface of the graft. The layer of fibrotic tissue prevents blood that leaks through the wall of the graft upon withdrawal of the dialysis needles to form a hematoma between the graft and surrounding tissue. This hematoma could cause adverse events such as lack of incorporation of the graft and increased chance for infection. Prior to the two week incorporation time, a central venous catheter (CVC) is often utilized to access the blood required for cycling through the dialysis machine. The CVC, however, exposes the patient to risks such as infection and the destruction of potential access sites distal to the CVC.

Self-sealing vascular access grafts have been designed that ostensibly do not require an extended period of time for healing and tissue growth before being punctured. Such grafts can be accessed sooner after surgery as shown, for example, in U.S. Pat. Nos. 4,619,641 and 5,116,360. Complete success has not been obtained from such grafts, however, since some still exhibit excessive leakage when punctured less than two weeks after being implanted. Additionally, some self-sealing grafts, due to their multi-layered construction, may be unable to distend sufficiently upon a change in arterial blood pressure. Furthermore, known self-sealing grafts may have a bulky construction that interferes with the sensing of blood pressure pulsation. Excessive structure in some self-sealing grafts acts to attenuate the blood pressure pulse and makes the search for the graft much harder for medical personnel attempting to establish a dialysis circuit.

Thus, there is a need for an early access, self-sealing, compliant and non-bulky AV graft for use with hemodialysis. The present invention meets these and other needs as described herein.

SUMMARY OF THE INVENTION

In one aspect of the invention, there is provided arteriovenous grafts which include a combination of layers which include a smooth antithrombogenic inner blood-contacting lumen, a porous outer-most textile layer which encourages tissue ingrowth and incorporation by the body and a self-sealing biocompatible inner layer therebetween.

In another aspect of the invention, there is provided a self-sealing arteriovenous graft having a tube including a polymeric inner layer defining a lumen through which blood may flow, an outer textile layer concentrically disposed about the inner layer and an intermediate self-sealing layer concentrically positioned between the inner and outer layers, the self-sealing layer including a biocompatible polymer.

Furthermore, the invention provides a self-sealing arteriovenous graft including a tube having a polymeric inner layer defining a lumen through which blood may flow, the inner layer including ePTFE; an outer knit layer concentrically disposed about the inner layer, the outer layer including polyethylene terephthalate (polyester); and an intermediate self-sealing layer concentrically positioned between the inner and outer layers, the self-sealing layer including silicone elastomer.

DETAILED DESCRIPTION

Figure 1:
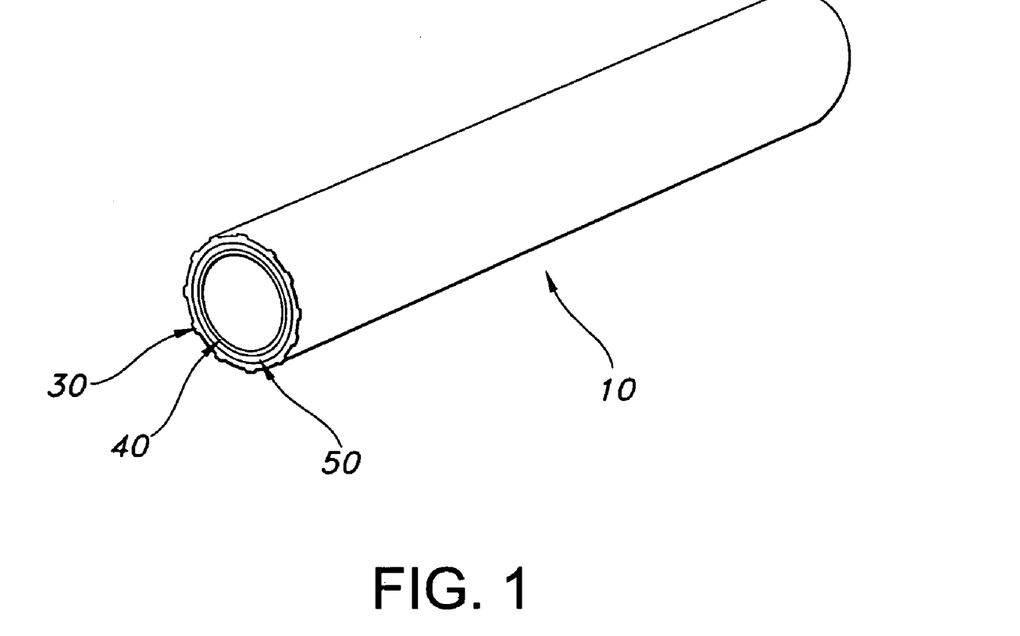
FIG. 1 is a perspective view illustrating an embodiment of a composite AV graft according to one arrangement of the present invention with an outer layer positioned over an intermediate layer and the intermediate layer positioned over an inner layer.
Figure 2:
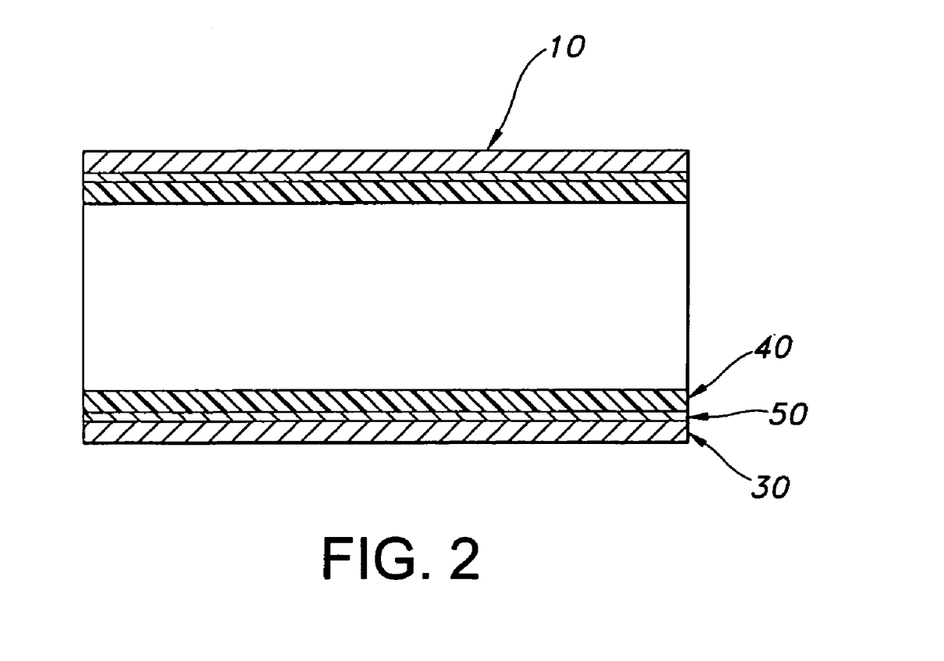
FIG. 2 is a longitudinal cross sectional view of the composite vascular graft in FIG. 1.

Referring to the drawings, there is shown in FIGS. 1 and 2, a composite arteriovenous access graft (AV access graft), generally designated as reference numeral 10. The AV graft 10 of the invention is ideally suited for use in chronic hemodialysis access, for example in a looped forearm AV graft, a looped thigh AV graft or any other AV graft application.

The AV graft 10 comprises an outer layer 30, an intermediate layer 50, and an inner layer 40. As shown in FIGS. 1 and 2, the intermediate layer 50 is uninterrupted circumferentially about, and in full face-to-face contiguous contact with, the inner layer 40.

In a desirable embodiment, outer layer 30 is constructed from biodegradable fibers. More desirably, outer layer 30 is made from alginate fibers.

In an even more desirable embodiment, calcium is added to the fibers comprising outer layer 30. The addition of calcium will act to decrease the clotting time of blood and provide for faster hemostasis of the AV graft 10 after needle removal.

In a particularly desirable embodiment, outer layer 30 is made from calcium alginate fibers. Methods for producing calcium alginate fibers are well known in the art. The extrusion of alginate solutions into an aqueous solution containing calcium ions to form calcium alginate filaments is known, for example, from British Patent Specifications Nos. 567,641; 568,177; 571,657 and 624,987, the disclosures of which are herein incorporated by reference.

In another arrangement, outer layer 30 is constructed from non-biodegradable fibers. More particularly, outer layer 30 may be made from polyvinyl alcohol fibers. Other non-biodegradable fibers may include polyester fibers such as polyethylene terephthalate (PET). Calcium may likewise be added to non-biodegradable fibers as well as biodegradable fibers to increase hemostasis.

In accordance with the invention, outer layer 30 is a textile layer. As used herein, the term "textile" is intended to mean graft substrates formed of woven, braided or knitted fabrics. Non-woven fabrics may be useful provided they enable sufficient suture retention and/or pull out strength. Non-woven fabrics made using methods known to those skilled in the art such as spin bonding and needle punch felting, may also be used. The yarns formed from the fibers used in constructing outer layer 30 may be flat, twisted, textured or non-textured or combinations thereof. A velour surface may also be incorporated. Additionally, the yarns may be monofilament, multifilament, staple or combinations thereof and may have high, low or moderate shrinkage properties or combinations thereof.

Figures 3, 4:
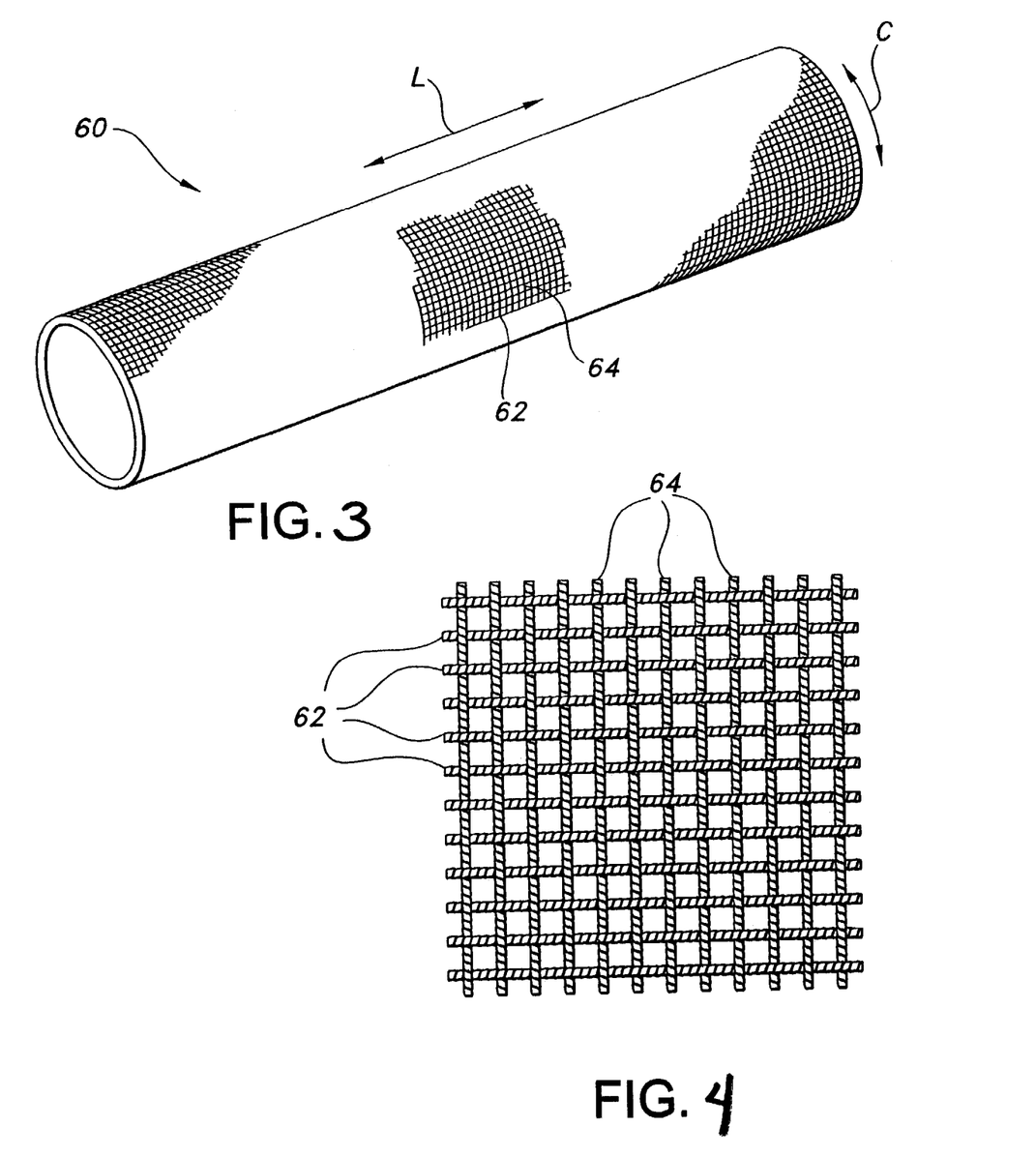
FIG. 3 is a perspective view of a woven tubular textile useful in the present invention.
FIG. 4 is a schematic showing of a conventional weave pattern useful in the woven tubular textile of FIG. 3.

In one example, FIGS. 3 and 4 depict an elongate woven hollow tubular textile 60. Any known weave pattern in the art, including, plain weave, satin weaves, basket weaves, twills, velours and the like may be used. The weave pattern includes warp yarns 62 running along the longitudinal length (L) of the woven textile and fill yarns 64 running around the circumference (C) of the textile. The warp yarns 62 are positioned approximately 90 degrees relative to the fill yarns 64. The textile typically flows from the machine in the warp direction. A simple weave is shown in FIG. 4 where adjacent warp yarns 62 and adjacent fill yarns 64 are interlaced in a one-up-one-down pattern.

Figure 5:
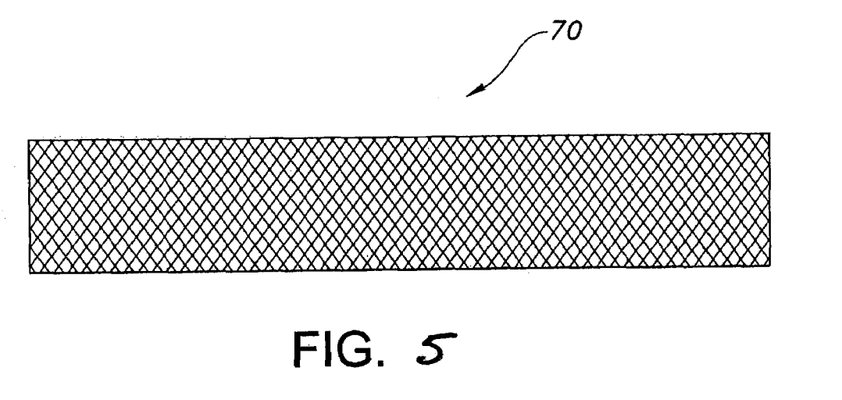
FIG. 5 is a side elevational view of a braided tubular textile useful in the present invention.
Figure 6:
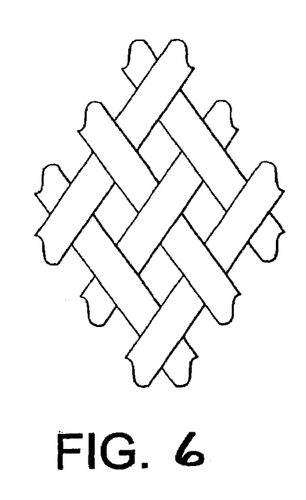
FIG. 6 is a schematic showing of a diamond braid useful in the braided tubular textile of FIG. 5.
Figure 7:
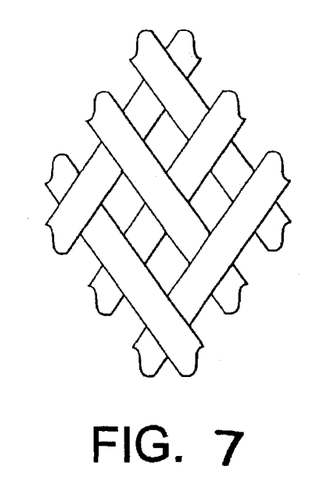
FIG. 7 is a schematic showing of a regular braid useful in the braided tubular textile of FIG. 5.
Figure 8:
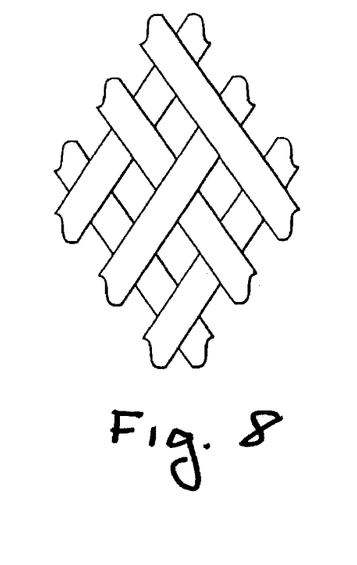
FIG. 8 is a schematic of a Hercules braid useful in the braided tubular textile of FIG. 5.

Braiding may also be used as shown, for example, in FIGS. 6 through 8 to form a hollow tubular braided textile portion 70 as depicted in FIG. 5. As depicted in FIG. 5, braiding of yarns includes the interlacing of at least two yarn systems such that the paths of the yarns are diagonal to the fabric delivery direction, forming either a flat or tubular structure. Useful braids include, but are not limited to, a diamond braid having a 1/1 intersection repeat as shown in FIG. 6, a regular braid having a 2/2 intersection repeat as shown in FIG. 7, or a Hercules braid having a 3/3 intersection repeat as shown in FIG. 8. Moreover, a triaxial braid may also be used. A triaxial braid, not shown, has at least one yarn that typically runs in the longitudinal direction or axial direction of the textile portion to limit yarn movement. The axial or longitudinal yarn is not interlaced or interwound with the other braid yarns, but is trapped between the different sets of yarns in the braided structure. Moreover, an interlocking three-dimensional braided structure or a multi-layered braided structure is also useful. A multi-layered braided structure is defined as a structure formed by braiding wherein the structure has a plurality of distinct and discrete layers. These layers may be bound by interlocking yarns or by adhesive laminates, sewing or the like.

Generally, a braided structure is formed having a braid angle from about 54.5° to about 90° with respect to the longitudinal axis of the braided structure, desirably about 54.5° to about 75°. The yarns of the braid tend to seek equilibrium at a braid angle of about 54.5°, which is a neutral angle for tubular vessels under pressure. Thus, when the braid angle is larger than the neutral angle, when pressure is exerted from within, for example due to fluid flow, the yarns will tend to scissor and decrease the braid angle thereby elongating or stretching the braided structure in order to reach the neutral angle.

Figure 9:
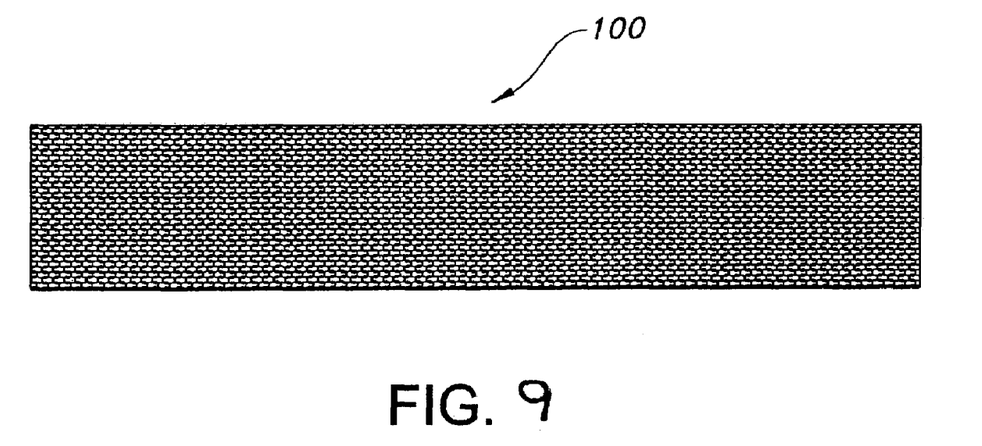
FIG. 9 is a side elevational view of a knitted tubular textile useful in the present invention.
Figure 10:
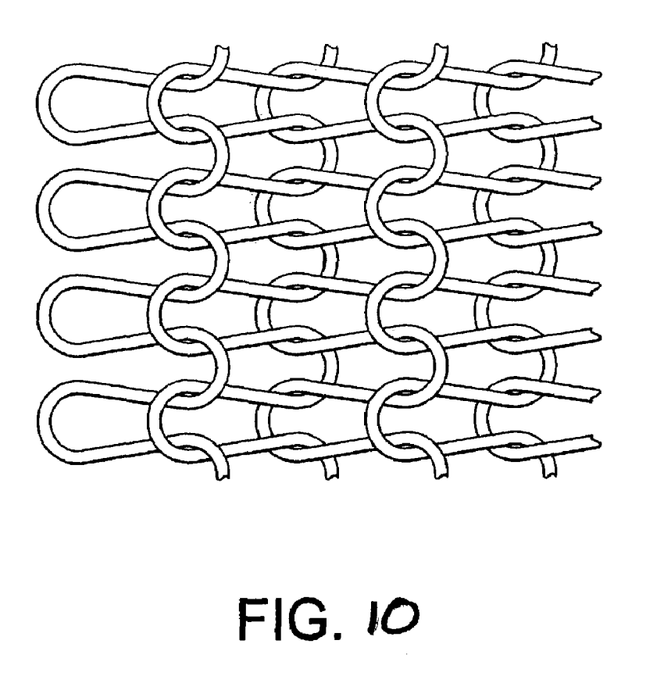
FIG. 10 is a schematic showing of a jersey weft knit useful in the knitted tubular textile of FIG. 9.

Additionally, a knitted textile member 100, as shown in FIGS. 9 and 10, may be used. Knitting involves the interlooping of one yarn system into vertical columns and horizontal rows of loops called wales and courses, respectively, with fabric coming out of the machine in the wale direction. A nonlimiting example of a knitted textile pattern, such as jersey weft knit, is depicted in FIG. 10. Warp knit patters such as tricot or double tricot are also desirable.

The yarn denier, which represents the linear density of the yarn, is desirably selected for durability and flexibility of the graft. The yarns used with the present invention may have a denier from about 1 to about 1000, more desirably from about 10 to about 100, and even more desirably from about 20 to about 60.

The use of a textile layer is advantageous due to the increased flexibility, durability and strength such a layer provides. For example, PET may be fabricated into a tubular textile by knitting, weaving, braided or non-woven techniques, to form a durable and compliant reinforcing outer layer 30. The use of such a material from which to form the outer layer 30 in the three layered system of the present invention advantageously provides a strengthened, yet flexible graft 10, which is readily incorporated by the body.

Once outer textile layer 30 is formed, it may be placed on a mandrel and heat-set into a tube with a cross section of generally circular shape. Prior to heat-setting, the textile is formed into a seamless tubular graft and heatset if it is comprised of a thermoplastic material such as polyester. Heatsetting may be achieved by submitting the textile layer to moderate temperatures, such as 190° F. to 400° F.

Inner layer 40 is fabricated from a biocompatible polymeric material, preferably, expanded polytetrafluoroethylene (ePTFE). Expanded PTFE may be constructed using any method known in the art, such as from CD 123 fine powder PTFE resin (ICI Americas) as taught in U.S. Pat. No. 3,953,566 to Gore, the disclosure of which is incorporated herein by reference.

In a particularly desirable embodiment, inner layer 40 is formed into a tube made from expanded polytetrafluoroethylene (ePTFE). The method of making an ePTFE tube by paste extrusion and expansion of the extrudate is well known in the art. Expanded PTFE is comprised of characteristic nodes and fibrils interconnecting the nodes. Interstices between the nodes and fibrils form pores which exist throughout the material matrix of the ePTFE. Expanded PTFE vascular grafts have met with considerable acceptance due, in large part, to their biocompatibility and handling characteristics.

The intermediate layer 50 of the AV graft of the invention is desirably made from a biocompatible elastomeric polymer or other biocompatible non-elastomeric materials, foamed polymers and other materials which contribute to hemostasis.

Additionally, any drug or bio-therapeutic agent may be coated or incorporated into this layer. Examples of suitable drugs or bio-therapeutic agents may include, without limitation, hemostatic agents, antibiotic agents, anti-tumor agents, cell cycle regulating agents, their homologs, derivatives, fragments, pharmaceutical salts and combinations thereof. Thrombo-resistant agents may be added to the inner layer 40 to increase patency of the graft. Useful thrombo-resistant agents may include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antibiotics may include, for example, penicillins, cephalosporins, vancomycins, amninoglycosides, quinolones, polymyxins, erythromycins, tetracyclines, chloramphenicols, clindamycins, lincomycins, sulfonamides, their homologs, analogs, fragments, derivatives, pharmaceutical salts and combinations thereof.

Useful anti-tumor agents may include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and combinations thereof.

Useful anti-viral agents may include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and combinations thereof. Other useful anti-microbial agents may include silver-containing materials such as metallic silver, silver oxide and silver phosphate.

Elastomeric polymers are herein defined as those polymers which at room temperature can be stretched under low stress to at least about twice their original length and upon release of the stress will recover with force to their approximate original length. When choosing an elastomeric polymer for intermediate layer 50, the desire for low kink diameter should be balanced against the thickness and modulus of the elastomeric intermediate layer; the objective being to select the minimum thickness necessary to prevent significant blood leakage through the access sites while maintaining acceptable handling characteristics. Biocompatible elastomeric polymers suitable for the intermediate layer 50 may include, but not be limited to copolymers, block polymers, silicone elastomers, polyurethane elastomers, polyurethane-carbonates or combinations thereof with a preferred thickness of the layer being about 0.01 mm to 10 mm, and more desirably about 0.1 mm to about 3 mm. When silicone is used as the intermediate layer, the desired thickness ranges from about 0.5 mm to 0.75 mm.

In another embodiment, the biocompatible polymer layer 50 is biodegradable. Desirable biodegradable materials useful for the intermediate layer 50 include but are not limited to trimethylene carbonate, polyethylene glycol, polypropylene glycol, polylactide/polyglycolide polymers, collagen and alginate.

Once the three layers have been fabricated, the composite AV graft 10 can be formed by any desirable method known in the art. For example, a tube formed from the intermediate layer 50 can be concentrically positioned over a tube formed from the inner layer 40 and the outer textile layer 30 subsequently can be concentrically positioned over the intermediate layer to form graft 10. Alternatively, inner layer 40 can be positioned on a mandrel and the mandrel suspended in a mold. Intermediate layer 50 of silicone rubber, for example, may be formed by pumping liquid silicone rubber into the mold and curing the liquid silicone rubber to form a solid rubber tube, thus insert molding intermediate layer 50 around inner layer 40. Outer layer 30 would then be positioned around inner layer 40.

Inner layer 40 can have an internal diameter from about 4 mm to 8 mm with 5 mm to 7 mm being the preferred internal diameter and a wall thickness of about 0.01 mm to about 2.0 mm, and most desirably about 0.25 mm to about 0.75 mm. The intermediate layer 50 can have a thickness of about 0.01 mm to about 2 mm preferably about 0.1 mm to about 1 mm. The outer tube can have a wall thickness of 0.5 to 3 mm, most preferably about 1 to 2 mm. The wall thickness of the inner and outer tubes may be the same or different.

Figure 11:
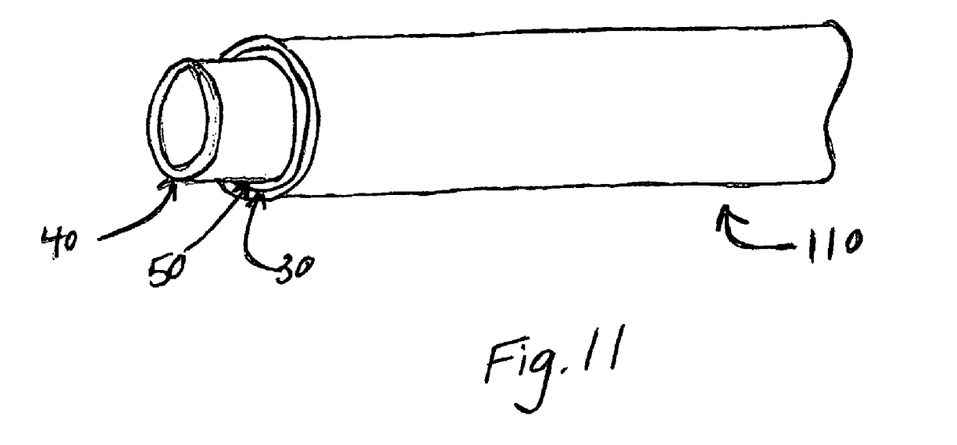
FIG. 11 is a perspective view illustrating an embodiment of a composite AV graft according to one arrangement of the present invention with an outer layer that is shorter than the inner layer.

The length of an inner tube formed from inner layer 40 depends on the specific application for the graft, and the site in the patient at which the tube is implanted. As a result, the inner tube can vary in length from about 100 mm to 500 mm, with about 250-450 mm being the most preferred range of length for looped forearm grafts. The length of the outer tube is equal to or less than that of the inner tube and can vary in length from 10 mm to 500 mm, with about 250-450 mm being the preferred length for forearm grafts. FIG. 11 depicts an AV graft 110 in which the outer layer 30 is shorter than the inner layer 40, thereby allowing the ends of the inner layer 40 to extend beyond each of the ends of the outer layer 30. The intermediate layer 50 is positioned between the two tubular layers and does not extend beyond both layers.

Figure 12:
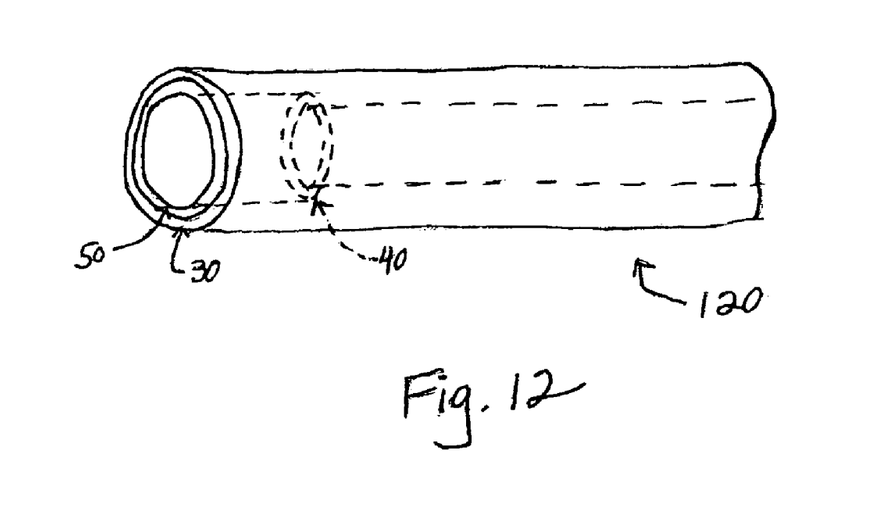
FIG. 12 is a perspective view illustrating an embodiment of a composite AV graft according to one arrangement of the present invention with an inner layer that is shorter than the outer layer.

Alternatively, the length of an inner tube formed from inner layer 40 is equal to or less than that of an outer tube formed from the outer layer 30 and can vary in length from 10 mm to 500 mm, with about 250-450 mm being the preferred length for forearm grafts. FIG. 12 depicts an AV graft 120 in which the inner layer 40 is shorter than the outer layer 30, thereby allowing the ends of the outer layer 30 to extend beyond each of the ends of the inner layer 40. By preventing the outer layer and/or middle layer from extending all the way to the ends of the graft 10, medical personnel can perform anastomoses on the end of graft 10 which will exhibit the same tactile properties as a conventional ePTFE graft.

EXAMPLES

Example 1

Increased Suture Retention Strength of ePTFE Grafts With a Knitted Covering

Four ePTFE grafts were compared to an ePTFE graft having a knitted covering to determine if the knitted covering resulted in increased suture retention strength. Suture retention strength refers to the force necessary to pull a suture from a sample prosthesis or to cause the wall of a prosthesis to fail.

The Exxcel™ soft graft (6 mm SW, Boston Scientific, Boston, Mass.), the Exxcel™ graft (6 mm SW Boston Scientific, Boston, Mass.), Impra (6 mm SW, Droitwich, UK) and Gore grafts (6 mm SW, Gore Enterprises Holdings, Inc, Newark, Del.) were used in comparison to a graft having a knitted covering. Suture retention strength was examined for each of the grafts by using a longitudinal procedure and an oblique procedure as described below.

Longitudinal Procedure. Each prosthesis was cut normal to the long axis. A suture was inserted 2 mm from the end of the stretched prosthesis through one wall of the prosthesis to form a half loop. The suture was pulled at the rate of 150 mm per minute. The force required to pull the suture through the prosthesis or cause the wall of the prosthesis to fail was recorded (measured in grams). All tests were performed according to the requirements described by the Association for the Advancement of Medical Instrumentation.

Oblique Procedure. The prostheses were cut at 45° to the long axis. Sutures were placed at the base (heel) of the cut. The force required to pull the suture though the prostheses or cause the wall of the prostheses to fail was recorded in grams for each sample prosthesis.

The results of both procedures are described below in Table 1.

TABLE 1

SUTURE RETENTION STRENGTH

|  |  | Longitudinal (grams) | Oblique (grams) |
|---|---|---|---|
| Exxcel | mean | 627 | 601 |
|  | std. dev. | 51 | 61 |
|  | n | 81 | 81 |
| Exxcel Soft | mean | 425 | 477 |
|  | std. dev. | 45 | 57 |
|  | n | 27 | 27 |
| Impra | mean | 312 | 330 |
|  | std. dev. | 64 | 47 |
|  | n | 4 | 4 |
| Gore | mean | 409 | 432 |
|  | std. dev. | 48 | 45 |
|  | n | 16 | 16 |
| ePTFE Graft With Knit Covering | mean | 1607 | 1621 |
|  | std. dev. | 133 | 170 |
|  | n | 12 | 13 |

These results confirm that a graft having textile covering in accordance with the present invention, such as the knitted covering used in sample 5, significantly improve the suture retention strength of prostheses when using either the oblique or longitudinal procedure.

Example 2

Durability of ePTFE Grafts Having an Outer Knit Covering Measured By Repeated Puncture The five grafts described above were additionally tested for durability using a repeated puncture test. This test is intended to determine the strength of a prosthesis after repeated puncture to simulate dialysis use. Samples are punctured repeatedly and then tested for pressurized burst strength.

A 16 gauge dialysis needle was used to puncture the sample prostheses 8, 16 and 24 times per square centimeter of the prostheses' external surface area. These values correspond to approximately 6, 12 and 18 months of clinical use. This assumes 6 punctures per week on one-third of the outer surface area of a 30 cm long prosthesis.

After the repeated puncturing, the sample prostheses were distended by either filling the prostheses directly with fluid or placing a balloon inside them and filling the balloon with fluid at a measured rate of pressure change until bursting of the sample prostheses took place. The results of this test are shown in Table 2.

TABLE 2

REPEATED PUNCTURE (BURST PRESSURE)

|  |  | 6 months (psi) | 12 months (psi) | 18 months (psi) |
|---|---|---|---|---|
| Exxcel | mean | — | 65 | 58 |
|  | std. dev. | — | 13 | 11 |
|  | n | — | 81 | 81 |
| Exxcel Soft | mean | — | 49 | 47 |
|  | std. dev. | — | 5 | 4 |
|  | n | — | 27 | 27 |
| Impra | mean | — | 36 | 32 |
|  | std. dev. | — | 0 | 1 |
|  | n | — | 2 | 2 |
| Gore | mean | — | 49 | 45 |
|  | std. dev. | — | 8 | 2 |
|  | n | — | 2 | 2 |
| ePTFE Graft With Knit Covering | mean | 93 | 85 | 80 |
|  | std. dev. | 9.9 | 15.8 | 7.8 |
|  | n | 12 | 12 | 12 |

The results from Table 2 clearly show that a graft having an outer knitted covering in accordance with the present invention, significantly increases the durability of a prosthesis as measured by a repeated puncture procedure.

Having described the preferred embodiments herein, it should be appreciated that that variations may be made thereto without departing from the contemplated scope of the invention. Accordingly, the preferred embodiments described herein are intended to be illustrative rather than limiting the true scope of the invention being set forth in the claims appended hereto.

We claim:

1. A self-sealing arteriovenous access graft comprising:
  a polymeric inner layer defining a lumen through which blood may flow;
  an outer textile layer concentrically disposed about the inner layer, said outer textile layer comprising biodegradable fibers comprising calcium alginate fibers; and
  an intermediate self-sealing tubular layer concentrically positioned between the inner and outer layers, said self-sealing layer being uninterrupted circumferentially about, and in full face-to-face contiguous contact with, said inner layer, said self-sealing layer comprising a biocompatible polymer, said self-sealing layer having a thickness of about 0.1 mm. to about 3 mm. which prevents blood leakage when punctured for dialysis,
  wherein said graft is configured to have a burst pressure of at least about 80 psi after repeated punctures for dialysis.

2. The graft according to claim 1, wherein said self-sealing layer is selected from the group consisting of silicone, polyurethane, polyurethane-carbonates and combinations thereof.

3. The graft according to claim 1, wherein said self-sealing layer comprises a silicone elastomer.

4. The graft according to claim 1, wherein said self-sealing layer comprises foamed polymer.

5. The graft according to claim 1, wherein said self-sealing layer further comprises a bio-therapeutic agent selected from the group consisting of thrombo-resistant agents, antibiotics, anti-tumor agents, anti-viral agents and combinations thereof.

6. The graft according to claim 1, wherein said self-sealing layer further comprises thrombo-resistant agents.

7. The graft according to claim 1, wherein said polymeric inner layer comprises ePTFE.

8. The graft according to claim 1, wherein the textile outer layer is selected from the group consisting of a knitted layer, a woven layer, a braided layer and a non-woven layer.

9. The graft according to claim 1, wherein the textile outer layer is a knitted layer.

10. The graft according to claim 9, wherein the knitted layer is warp knitted.

11. The graft according to claim 10, wherein the warp-knit is selected from the group consisting of a tricot and a double tricot pattern.

12. The graft according to claim 1, wherein said outer layer is shorter than said inner layer and is positioned over the center of the inner layer thereby allowing the ends of the inner layer to extend beyond each of the ends of the outer layer.

13. The graft according to claim 1, wherein said inner layer is shorter than said outer layer and is positioned over the center of the inner layer thereby allowing the ends of the outer layer to extend beyond each of the ends of the inner layer.

14. A self-sealing arteriovenous graft comprising:

a polymeric inner layer defining a lumen through which blood may flow, said inner layer comprising ePTFE;

an outer knit layer concentrically disposed about the inner layer, said outer layer comprising biodegradable fibers comprising calcium alginate fibers, and an intermediate self-sealing tubular layer concentrically positioned between the inner and outer layers, said self-sealing layer being uninterrupted circumferentially about, and in full face-to-face contiguous contact with, said inner layer, said self-sealing layer comprising a silicone elastomer, said self-sealing layer having a thickness of about 0.01 mm. to about 1.0 mm. which prevents blood leakage when punctured for dialysis, wherein said graft is configured to have a burst pressure of at least about 80 psi after repeated punctures for dialysis.

15. The graft according to claim 14, wherein said knit layer is of a pattern selected from the group consisting of tricot and double tricot.

16. The graft according to claim 14, wherein said self-sealing layer has a thickness of about 0.5 mm to about 0.75 mm.

\* \* \* \* \*